United States Patent

Klinkhammer et al.

[11] Patent Number: 5,977,381
[45] Date of Patent: Nov. 2, 1999

[54] PROCESS FOR MAKING 3-AMINO-PYROLIDINE DERIVATIVES

[75] Inventors: Uwe Klinkhammer, Hartheim, Germany; Paul Spurr, Riehen; Shaoning Wang, Basel, both of Switzerland

[73] Assignee: Hoffmann-La Roche Inc., Nutley, N.J.

[21] Appl. No.: 09/213,465

[22] Filed: Dec. 17, 1998

[30] Foreign Application Priority Data

Jan. 12, 1998 [EP] European Pat. Off. ............. 98100381

[51] Int. Cl.⁶ .................................................. C07D 207/14
[52] U.S. Cl. ........................................................ 548/557
[58] Field of Search ............................................ 548/557

[56] References Cited

U.S. PATENT DOCUMENTS

| | | | |
|---|---|---|---|
| 4,785,119 | 11/1988 | Hojo et al. ............................. | 548/557 |
| 4,916,141 | 4/1990 | Sanchez ................................. | 514/300 |
| 5,177,217 | 1/1993 | Van Le et al. ........................ | 548/557 |
| 5,703,244 | 12/1997 | Li et al. ................................. | 548/557 |

FOREIGN PATENT DOCUMENTS

| | | |
|---|---|---|
| 218 249 | 4/1987 | European Pat. Off. . |
| 391 169 | 10/1990 | European Pat. Off. . |
| 849 269 | 6/1998 | European Pat. Off. . |
| 07233146 | 9/1995 | Japan . |
| 08053412 | 2/1996 | Japan . |
| 9-124595 | 5/1997 | Japan . |
| 1392 194 | 4/1975 | United Kingdom . |

OTHER PUBLICATIONS

Chemical Abstracts, vol. 130, No. 2, abstract No. 13877 (1999).
Rosen et al., Asymmetric Synthesis and Properties of the Enantiomers of the Antibacterial Agent 7-(3-Aminopyrrolidin-1-yl)-1, 4-dihydro-6-fluoro-4-oxo-1, 8-naphthyridine-3-carboxylic Acid Hydrochloride, J. Med. Chem., 31, pp. 1586–1590, 1988.
Joseph P. Sanchez, et al., J. Med. Chem., 35, pp. 1764–1773, 1992.
Dialog Web Abstract EP 391169 (Oct. 10, 1990).
Dialog Web Abstract JP 9124595 (May 13, 1997).

*Primary Examiner*—Johann Richter
*Assistant Examiner*—Jane C. Oswecki

*Attorney, Agent, or Firm*—George W. Johnston; Patricia S. Rocha-Tramaloni; Eileen M. Ebel

[57] ABSTRACT

The invention is concerned with a process for making a compound of formula

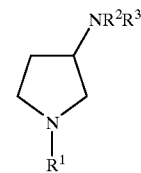

I wherein $R^1$ is hydrogen, alkyl, cyclo-alkyl, alkenyl, aryl or an amino protecting group; and $R^2$, $R^3$ each independently is hydrogen, alkyl, cyclo-alkyl, alkenyl or aryl; by reacting a compound of the formula

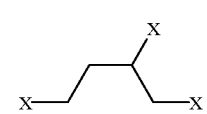

II wherein

X is a protected hydroxy group; with $R^1NH_2$ to form a compound of formula

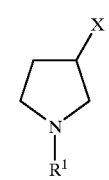

III wherein X and $R^1$ are described herein above; and then reacting the compound of formula III with $R^2R^3NH$ under pressure to form the compound of formula I. These compounds are valuable intermediates useful in making cephalosporin derivatives.

13 Claims, No Drawings

PROCESS FOR MAKING 3-AMINO-PYROLIDINE DERIVATIVES

BACKGROUND OF THE INVENTION

The present invention is concerned with a novel process for making racemic and optically active 3-amino-pyrrolidine derivatives and with the use of this process in making cephalosporin derivatives.

3-Amino-pyrrolidine derivatives, especially optically active 3-amino-pyrrolidine derivatives, are important intermediates for the production of agrochemicals and of pharmaceutically active substances such as, for example, of vinylpyrrolidinone-cephalosporin derivatives.

3-Amino-pyrrolidine derivatives can be made by known methods, for example as described in EP-A 0 218 249 starting from 1,2,4-trisubstituted butane derivatives such as e.g. tribromobutane or trihydroxybutane. The racemic derivatives can then, if desired, can be converted by a racemate resolution into optically active 3-amino-pyrrolidine derivatives as described in, JP 09124595-A. A process for the manufacture of optically active 3-amino-pyrrolidine derivatives based on the conversion of 4-hydroxy-proline as described, for example, in *J. Med. Chem.* 1764(92), 35, gives optically active 3-aminopyrrolidine over 3 steps.

The known methods for making 3-aminopyrrolidine derivatives as described, for example, in UK Patent No. 1 392 194, EP 0 391 169 and U.S. Pat. No. 4 916 141, are time consuming and lead to expensive intermediates. The interest in other processes for making 3-amino-pyrrolidine derivatives, especially of optically active 3-amino-pyrrolidine derivatives, is therefore extremely high. It has now been found that 3-amino-pyrrolidine derivatives, especially optically active 3-amino-pyrrolidine derivatives, can be made in high yields in a simple manner from 1,2,4-trihydroxybutane derivatives.

SUMMARY OF THE INVENTION

The invention is accordingly concerned with a process for making a compound of formula I

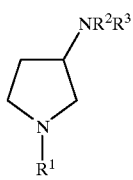

wherein
$R^1$ is hydrogen, alkyl, cyclo-alkyl, alkenyl, aryl or an amino protecting group; and
$R^2, R^3$ each independently is hydrogen, alkyl, cyclo-alkyl, alkenyl or aryl; which comprises (a) reacting a compound of formula II

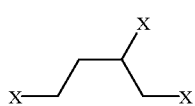

wherein
X is a protected hydroxy group; with $R^1NH_2$ to form a compound of formula III

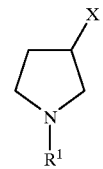

wherein X is a protect d hydroxy group and $R^1$ is hydrogen, alkyl, cyclo-alkyl, alkenyl, aryl or an amino protecting group;
(b) reacting the compound of formula III with $R^2R^3NH$ under pressure to form the compound of formula I.

DETAILED DESCRIPTION OF THE INVENTION

The present invention is concerned with a process for making a compound of formula

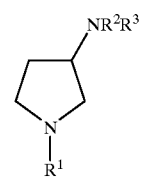

wherein
$R^1$ is hydrogen, alkyl, cyclo-alkyl, alkenyl, aryl or an amino protecting group; and
$R^2, R^3$ each independently is hydrogen, alkyl, cyclo-alkyl, alkenyl or aryl; which comprises (a) reacting a compound of formula II

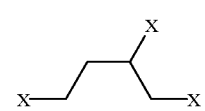

wherein
X is a protected hydroxy group; with $R^1NH_2$ to form a compound of formula III

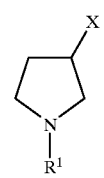

wherein X is a protected hydroxy group and $R^1$ is hydrogen, alkyl, cyclo-alkyl, alkenyl, aryl or an amino protecting group;
(b) reacting the compound of formula III with $R^2R^3NH$ under pressure to form the compound of formula I.

The term "protected hydroxy group" embraces in the scope of the present invention ester groups, for example, sulphonates such as mesylate, tosylate p-bromobenzenesulphonate or p-nitrobenzenesulphonate. These are especially groups which are cleaved off selectively under the reaction conditions for the ring closure in the presence of an amine of the formula NH₂R such that the protected hydroxy group X in the 2-position is not liberated. Mesylate and tosylate are especially preferred protected hydroxy groups X.

The term "amino protecting group" embraces in the scope of the present invention alkyl, benzyl, alkenyl, alkyloxycarbonyl, alkenyloxycarbonyl, benzyloxycarbonyl and the like. Allyl, benzyl, tert-butyloxycarbonyl, allyloxycarbonyl and benzyloxycarbonyl are especially preferred.

The term "alkyl" embraces in the scope of the present invention straight-chain and branched, hydrocarbon groups with 1 to 12, especially 1 to 8, carbon atoms such as, for example, methyl, ethyl, propyl, butyl, pentyl, hexyl, heptyl, octyl, i-propyl, i-butyl, tert-butyl, 2-methylbutyl, and the like. The alkyl groups may be optically active; that is, have a chiral center.

The term "alkenyl" embraces in the scope of the present invention unsaturated, straight-chain and branched hydrocarbon groups with 3 to 12, especially 3 to 8 carbon atoms such as, for example, allyl, butenyl, pentenyl, and the like.

The term "cyclo-alkyl" embraces in the scope of the present invention cyclic hydrocarbon groups with 3 to 8 carbon atoms such as, for example, cyclo-propyl, cyclo-butyl, cyclo-pentyl, cyclo-hexyl, cyclo-heptyl and cyclo-octyl.

The term "aryl" embraces in the scope of the present invention aromatic hydrocarbon groups which are unsubstituted or substituted with one or more alkyl or halogen groups such as, for example, phenyl, tolyl and naphthyl, as well as aromatic 6-ring heterocycles such as, for example, pyridine, pyrimidine and pyridazine.

The process in accordance with the invention is especially suitable for making optically active 3-amino-pyrrolidine derivatives of the formulae

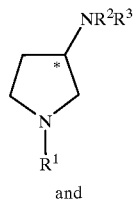

I-a and

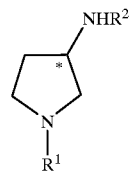

I-1a

The process is distinguished over known processes primarily in that on the one hand by virtue of the use of a chiral educt of the formula

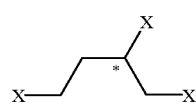

II-a the racemate resolution is no longer necessary and on the other hand the number of steps making the 3-amino substituted pyrrolidine derivative of the formulae I-a and I-1a, especially 3-amino-pyrrolidine derivatives of formula I-a in which $R^2$ and $R^3$ are each hydrogen which proceeds with high optical and chemical yields, is reduced by appropriate choice of the protecting groups.

In an especially preferred aspect of the process, optically active butyl-1,2,4-trimesylate (methanesulphonic acid 3-methanesulphonyloxy-1-methanesulphonyloxy-methyl-propyl ester) is converted in the presence of a primary amine $R^1NH_2$, wherein $R^1$ is benzyl, in tetrahydrofuran at a temperature of from about 0° C. to about 70° C., preferably at about 50 to about 60° C., into the corresponding optically active pyrrolidine derivative of formula III; the amino protecting group $R^1$(benzyl) in the pyrrolidine derivative of formula III is replaced in the presence of allyl haloformate by allyloxycarbonyl in an inert solvent such as a hydrocarbon e.g. heptane, at temperatures of from about 0 to about 100° C., preferably from about 30 to about 70° C.; subsequently the desired optically active 3-amino-pyrrolidine derivative of formula I-a or I-1a is obtained by introducing the amino group in the presence of $R^2R^3NH$, optionally in a solvent, such as e.g. tetrahydrofuran or dimethoxyethane, under pressure, preferably under a pressure of from about 30 to about 200 bar, especially under a pressure of from about 50 to about 80 bar, at a temperature of from about 20 to about 200° C., preferably from about 100 to about 150° C.

The process in accordance with the invention is especially suitable for making optically active 1-allyloxy-3-amino-pyrrolidine, an intermediate for the production of vinylpyrrolidinone-cephalosporin derivatives of the formula

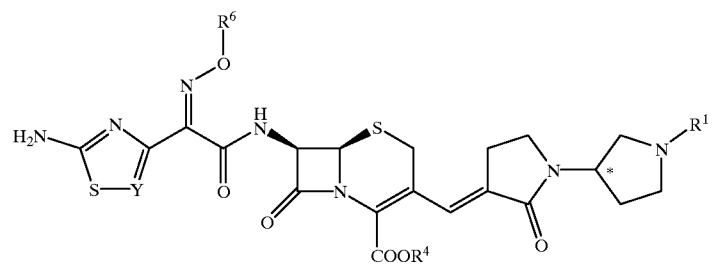

A wherein
Y is CH or nitrogen;
R⁶ is hydrogen or alkyl;
R⁴ is hydrogen, an alkali metal ion or a tertiary ammonium group or an acid protecting group;
R¹ is hydrogen, alkyl or an amino protecting group;
* denotes a centre of chirality.

Compounds of formula A are cephalosporin derivatives having a high antibacterial activity, especially against methicillin-resistant strains of *Staphylococcus aureus* (MRSA) and *Pseudomonas aeruginosa*.

Compounds of formula A can be made, for example, in a convergent synthesis as described in EP-A-849269 in accordance with Scheme I:

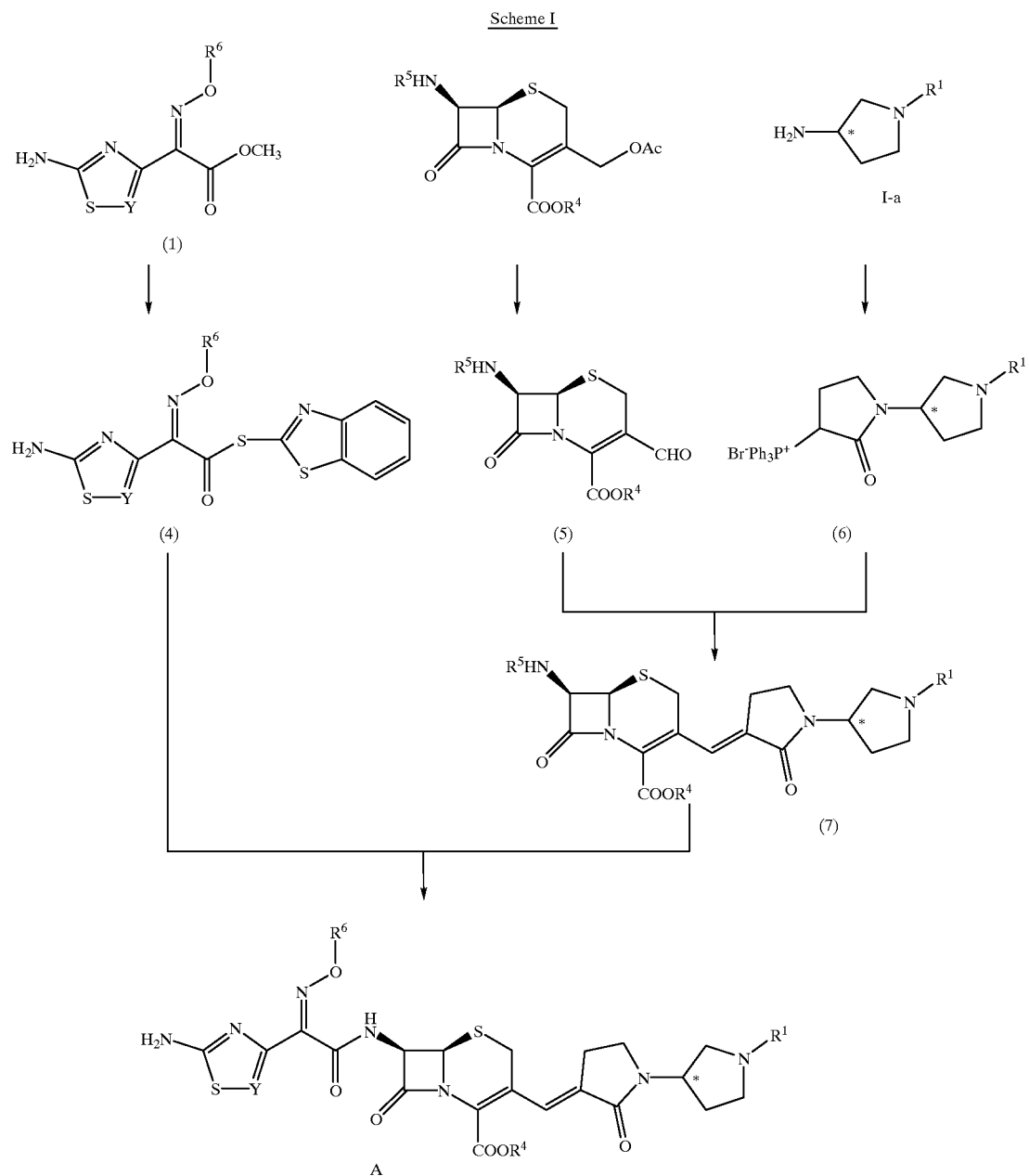

The symbols used in Scheme I (Y, $R^1$, $R^5$, and $R^6$) are as defined hereinabove and $R^5$ is an amino protecting group.

The 3-amino-pyrrolidine derivative of formula I-a in which $R^2$ and $R^3$ is hydrogen is made in accordance with the invention according to the method described above, thereafter reacted with chloro-2-bromobutyroyl chloride and the N-substituted 3-bromopyrrolidone is converted into the Wittig salt (6) which is reacted in accordance with Scheme I with the cephemaldehyde (5). The substituted cephem derivative (7) is then reacted with an activated acyl derivative (4) to give the vinylpyrrolidinone-cephalosporin derivative of formula A.

Making the vinylpyrrolidinone-cephalosporin derivatives of formula A can be simplified by the use of the process in accordance with the invention, by which 3-amino-pyrrolidine derivatives of formula I-a and I-1a, especially 3-amino-pyrrolidine derivatives of formula I-a in which $R^2$ and $R^3$ each are hydrogen, are accessible with high chemical and optical yields.

The present invention relates to the aspects described above and especially also to the use of the process for making the compounds of formula I and of the compounds of formula A, which are made according to the said processes.

The following Examples serve only to illustrate the invention and have no limiting character.

EXAMPLE 1

Preparation of methanesulphonic acid 3,4-bis-methanesulphonyloxy-butyl ester

A solution of 18.1 ml of methanesulphonic acid in 45 ml of ethyl acetate was added dropwise within 2 hours under argon to a solution, cooled to 0–5° C., of 7.96 g of S-1,2,4-butanetriol and 33.5 ml of triethylamine in 90 ml of ethyl acetate. The white suspension was stirred at 0–5° C. for a further 2 hours and thereafter the suspension was filtered and the yellow filtrate was washed in succession with 75 ml of 1N hydrochloric acid, 75 ml of saturated $NaHCO_3$ solution and 75ml of saturated NaCl solution. The organic phase was dried over $Na_2SO_4$, filtered and the filtrate was concentrated. 21.79 g of yellow oil were obtained.

EXAMPLE 2

Preparation of methanesulphonic acid (S)-1-benzyl-pyrrolidin-3-yl ester a) 21.8 ml of benzylamine were added dropwise to a solution of 17 g of methanesulphonic acid 3,4-bis-methanesulphonyloxy-butyl ester (from Example 1) in 200 ml of tetrahydrofuran under argon, with the solution warming to 30° C. The solution was boiled at reflux for 24 hours, thereafter cooled to 0–5° C. and the benzylammonium salt which thereby precipitated was filtered off. The filtrate was concentrated, the residude was taken up in 150 ml of tert-butyl methyl ether and the emulsion which thereby resulted was saturated with dry ice. After 5 minutes the white slurry was dissolved with 150 ml of water. The organic phase was separated and washed with 50 ml of saturated NaCl solution and with 30 ml of saturated NaCl solution. The washed solution was extracted with 100 ml of tert-butyl methyl ether and the organic phases were combined, dried with $Na_2SO_4$, filtered and the filtrate was concentrated. 12 1 g of yellow oil were obtained.

b) 13.8 g of sodium hydride were suspended in 250 ml of tetrahydrofuran under argon and cooled to 0–5° C. Within 1.5 hours there was added dropwise to this suspension a yellow solution of 88.6 g of N-benzyl-3-S-pyrrolidinol in 500 ml of tetrahydrofuran, the mixture was stirred at 0–5° C. for 15 minutes and treated dropwise within 2 hours with a solution of 42.74 ml of mesyl choride in 250 ml of tetrahydrofuran. After stirring at 0–5° C. for 1 hour the suspension was filtered over speedex, the filtrate was concentrated and the oily residue was taken up in 1000 ml of tert-butyl methyl ether and 280 ml of 3N sodium hydroxide solution. The phases were separated, the organic phase was washed with 250 ml of sodium hydroxide solution. The phases were separated, the organic phase was washed with 250 ml of sodium hydroxide solution and the wash solution was extracted with 500 ml of tert-butyl methyl ether. The organic phases were combined, dried over $Na_2SO_4$, filtered and the filtrate was concentrated. There were obtained 103.24 g of brown oil which was purified by chromatography. 51.44 g of product were obtained.

EXAMPLE 3

Preparation of allyl-3-methanesulphonyloxy-pyrrolidine-1-carboxylate 6.4 ml of allyl chloroformate were added dropwise to 10.2 g of methanesulphonic acid (S)-1-benzyl-pyrrolidin-3-yl ester in 880 ml of n-heptane at room temperature within 10 minutes under argon and with slight cooling. The two-phase mixture was stirred vigorously for 2 hours 45 minutes and subsequently treated with 40 ml of methanol/water (1:1). The aqueous methanolic phase was separated, extracted with 40 ml of heptane and thereafter the methanol was distilled off on a rotary evaporator. The aqueous phase was extracted twice with 30 ml of ethyl acetate. The organic phases were combined, dried over $Na_2SO_4$, filtered and the filtrate was concentrated. 8.23 g of beige oil were obtained.

EXAMPLE 4

Preparation of allyl 3-amino-pyrrolidine-1-carboxylate 1 g of allyl 3-methanesulphonyloxy-pyrrolidine-1-carboxylate was placed in an autoclave, evacuated 4 times under argon and again exposed to air and subsequently cooled in an acetone/$CO_2$ bath. The reaction was effected at 80 bar with ammonia at a temperature of 110° C. After stirring for 90 minutes the autoclave was cooled, the residue was taken up in methylene chloride, the suspension was filtered and the filtrate was concentrated. There was obtained 0.68 g of pale brown oil with an e.e. (enantiomeric excess) of 96.7%.

EXAMPLE 5

Preparation of 1-benzyl-3-amino-pyrrolidine 1.94 g of methanesulphonic acid (S)-1-benzyl-pyrrolidin-3-yl ester were placed in an autoclave, evacuated 4 times under argon and again exposed to air, and then cooled in an acetone $CO_2$ bath. The reaction was effected at 80 bar with ammonia at a temperature of 110° C. After stirring for 150 minutes the autoclave was cooled, the residue was taken up in methylene chloride, the suspension was filtered and the filtrate was concentrated. 1.33 g of pale brown oil were obtained. After purification by chromatography there were obtained 1.26 g of product with an e.e. (enantiomeric excess) of 96.8/0%.

EXAMPLE 6

Preparation of benzyl (R)-3-amino-pyrrolidine-1-carboxylate a) Preparation of benzyl (S)-3-hydroxy-pyrrolidine-1-carboxylate The pH of a solution of 6.18 g of (S)-3-hydroxy-pyrrolidine hydrochloride in 175 ml of water was adjusted to 10 with 10% sodium hydroxide solution and cooled to 0°–5° C. 7.1 ml of benzyl chloroformate were added dropwise within 30 minutes under argon, with the pH of the solution being held between 9.5 and 11.5 by the dropwise addition of 10% sodium hydroxide solution. After completion of the addition the suspension was stirred at room temperature for 16 hours. The suspension was extracted with ethyl acetate, the organic phase was washed with water, dried over $Na_2SO_4$, filtered and the filtrate was concentrated. Purification of the crude product over a silica gel column gave 7.33 g of benzyl (R)-3-hydroxy-pyrrolidine-1-carboxylate as a beige liquid.

b) Preparation of benzyl (S)-3-methanesulphonyloxy-pyrrolidine-1-carboxylate

A solution of 7.3 g of benzyl (R)-3-hydroxy-pyrrolidine-1-carboxylate and 5.56 ml of triethylamine in 80 ml of ethyl acetate was cooled to 0–5° C. under argon and treated within 30 minutes with a solution of 2.97 ml of mesyl chloride in 20 ml of ethyl acetate. After stirring at room temperature for 2 hours and leaving to stand for 16 hours the suspension was diluted with 40 ml of water, stirred for 10 minutes and the organic phase was separated. The organic phase was extracted in succession with 20 ml of 1N HCl, 20 ml of saturated $NaHCO_3$ solution and 10 ml of saturated NaCl solution. The organic phase was dried over $Na_2SO_4$, filtered and the filtrate was concentrated to give 10.18 g of product as a beige oil.

c) Preparation of benzyl (R)-3-amino-pyrrolidine-1-carboxylate 5.0 g of benzyl (S)-3-methanesulphonyloxy-pyrrolidine-1-carboxylate were placed in an autoclave, evacuated four times under argon and cooled in an acetone/$CO_2$ bath. After the addition of ammonia the reaction was carried out at 136 bar at a temperature of 150° C. After stirring for 40 minutes the autoclave was cooled, the residue was taken up in methylene chloride, the suspension was filtered and the filtrate was concentrated. There were obtained 3.52 g of pale yellow oil, e.e. 97%.

EXAMPLE 7

Preparation of tert-butyl (R)-3-amino-pyrrolidine-1-carboxylate a) Preparation of tert-butyl (S)-3-hydroxy-pyrrolidine-1-carboxylate 34.1 g of (S)-3-hydroxy-pyrrolidinol hydrochloride and 29.2 g of $K_2CO_3$ were suspended in 400 ml of methanol under argon. The suspension was cooled to 0–5° C. and treated while stirring within 10 minutes with 45.8 g of di-tert-butyl dicarbonate. The reaction mixture was stirred firstly at 0–5° C. for 30 minutes and subsequently at room temperature for 4.5 hours. The suspension was concentrated and the residue was taken up in 400 ml of ethyl acetate and 200 ml of water. The organic was separated, washed with water, dried over $Na_2SO_4$, filtered and the filtrate was concentrated. There were obtained 34.1 g of product as a brownish liquid, which was used in the next step without purification.

b) Preparation of methanesulphonic acid (S)-1-carboxylic acid tert-butyl-pyrrolidin-3-yl ester 34.1 g of tert-butyl (S)-3-hydroxy-pyrrolidine-1-carboxylate and 29.2 ml of triethylamine were dissolved in 300 ml of ethyl acetate under argon and cooled to 0–5° C. before the dropwise addition within 30 minutes of 3.91 ml of mesyl chloride in 20 ml of ethyl acetate. The resulting suspension was stirred at 0–5° C. for 1.5 hours and subsequently at room temperature for 16 hours. The suspension was diluted with 150 ml of water, stirred for 10 minutes and the organic phase was separated. The organic phase was washed in succession with 1N HCl, saturated $NaHCO_3$ solution and saturated NaCl solution. The organic phase was dried over $Na_2SO_4$ and filtered. The filtrate was concentrated and gave 50.4 g of product as a beige liquid.

c) Preparation of tert-butyl (R)-3-amino-pyrrolidine-1-carboxylate 5.0 g of methanesulphonic acid (S)-1-carboxylic acid tert-butyl-pyrrolidin-3-yl ester were placed in an autoclave, evacuated four times under argon and cooled in an acetone/$CO_2$ bar. After the addition of ammonia the reaction was carried at 132 bar at a temperature of 150° C. After stirring for 2 hours the autoclave was cooled, the residue was taken up in methylene chloride, the suspension was filtered and the filtrate was concentrated. There were obtained 3.32 g of pale yellow oil, e.e. 97%.

We claim:

1. A process for making a compound of formula I

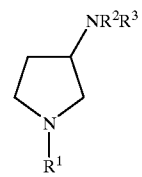

I wherein
$R^1$ is hydrogen, alkyl, cyclo-alkyl, alkenyl, aryl or an amino protecting group; and
$R^2, R^3$ each independently is hydrogen, alkyl, cyclo-alkyl, alkenyl or aryl; which comprises (a) reacting a compound of formula II

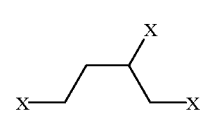

II wherein
X is a protected hydroxy group; with $R^1NH_2$ to form a compound of formula III

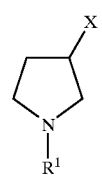

III wherein X is a protected hydroxy group and $R^1$ is hydrogen, alkyl, cyclo-alkyl, alkenyl, aryl or an amino protecting group;

(b) reacting the compound of formula III with $R^2R^3NH$ under pressure to form the compound of formula I.

2. The process of claim 1, wherein $R^3$ is hydrogen.

3. The process of claim 1, wherein process step (a) is carried out at a temperature of from about 0° C. to about 70° C.

4. The process of claim 3, wherein process step (b) is a carried out at a temperature of from about 20° C. to about 200° C. and at a pressure of from about 30 to about 200 bar.

5. The process of claim 3, wherein the temperature is from about 50° C. to about 60° C.

6. The process of claim 4, wherein the temperature is from about 100° C. to about 150° C.

7. The process of claim 6, wherein the pressure is from about 50 to about 80 bar.

8. The process of claim 2, wherein process step (a) is carried out at a temperature of from about 0° C. to about 70° C.

9. The process of claim 8, wherein process step (b) is a carried out at a temperature of from about 20° C. to about 200° C. and at a pressure of from about 30 to about 200 bar.

10. The process of claim 8, wherein the temperature is from about 50° C. to about 60° C.

11. The process of claim 9, wherein the temperature is from about 100° C. to about 150° C.

12. The process of claim 11, wherein the pressure is from about 50 to about 80 bar.

13. The process of claim 1, wherein the compound of formula II is

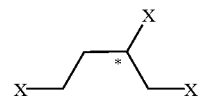

where * represents a chiral center.

* * * * *